United States Patent [19]

Wester

[11] Patent Number: 5,468,732

[45] Date of Patent: Nov. 21, 1995

[54] PHOSPHORUS CONTAINING RENIN INHIBITORS

[75] Inventor: Ronald T. Wester, Ledyard, Conn.

[73] Assignee: Pfizer Inc., New York, N.Y.

[21] Appl. No.: 741,442

[22] PCT Filed: Feb. 16, 1989

[86] PCT No.: PCT/US89/00636

§ 371 Date: Aug. 2, 1991

§ 102(e) Date: Aug. 2, 1991

[87] PCT Pub. No.: WO90/09172

PCT Pub. Date: Aug. 23, 1990

[51] Int. Cl.$^6$ ............... A61K 38/00; C07F 9/02; C07F 9/22; C07F 9/36
[52] U.S. Cl. ............... 514/19; 530/800; 558/170; 562/14; 562/15; 568/15; 564/12; 564/14
[58] Field of Search ............... 514/19; 530/800; 558/170; 562/14–15; 568/15; 564/12, 14

[56] References Cited

U.S. PATENT DOCUMENTS

| | | |
|---|---|---|
| 4,016,148 | 4/1977 | Atherton et al. . |
| 4,128,542 | 12/1978 | Atherton et al. . |
| 4,143,134 | 3/1979 | Atherton et al. . |
| 4,250,085 | 2/1981 | Atherton et al. . |

FOREIGN PATENT DOCUMENTS

| | | |
|---|---|---|
| 0249445 | 12/1987 | European Pat. Off. . |
| 0266950 | 5/1988 | European Pat. Off. . |
| 331105 | 9/1989 | European Pat. Off. ........... 514/19 |

OTHER PUBLICATIONS

Murphy et al, Amino Acids, Chemistry, Biology and Medicine, ESCOM Publishers, 1990 pp. 677–688.
M. C. Allen et al., J. Med. Chem., 1989, 32, pp. 1652–1661.
R. Guegan et al., J. Med. Chem., 1986, 29, pp. 1152–1159.
J. F. Dellaria et al., Tet. Lett., vol. 27, No. 21, pp. 2337–2340, 1986.
Greenlee Pharm Res. vol. 4 (1987) pp. 364–374.
Repine et al. J. Med. Chem. (1991) 34, 1935–1943.
Burger et al. *Medicinal Chem* 3rd ed. 1021–1052 (1970).
Burger et al. *Med. Chem* 4th ed. 288–89 (1981).
Dellaria et al. Tet. Lett vol. 27 No. 21 pp. 2337–2340 (1986).
Burger, Med. Chem. (2nd ed) Interscience Publishers, N.Y. (6/60) pp. 565–581, 600–601.
Kokubu et al. Biochem. Pharm. vol. 22 (1973) 3217–23 (1973).
Plattner et al. J. Med. Chem. 31(12) 2277–88 (1988).
Bolis et al. J. Med. Chem. 30(10) pp. 1729–1737 (1987).

*Primary Examiner*—Jill Warden
*Assistant Examiner*—Sheela J. Huff
*Attorney, Agent, or Firm*—Peter C. Richardson; Gregg C. Benson; John D. Conway

[57] ABSTRACT

Phosphorus containing polypeptides as renin inhibitors, useful as antihypertensive agents.

15 Claims, No Drawings

PHOSPHORUS CONTAINING RENIN INHIBITORS

BACKGROUND OF THE INVENTION

The proteolytic enzyme renin, which has a molecular weight of about 40,000, is produced in and secreted into the blood by the kidney. It is known to be active in vivo in cleaving the naturally-occurring plasma glycoprotein angiotensinogen, in the case of human angiotensinogen at the bond between the leucine (10th) and valine (11th) amino acid residues at the N-terminal end of the angiotensinogen:

Asp—Arg—Val—Tyr—Ile—His—Pro—Phe—His—Leu—Val—
 1    2    3    4   5    6    7    8    9    10   11

Ile—His—Ser—Glu—
12   13   14   15

The circuiting N-terminal decapeptide (angiotensin I) formed by the above cleaving action of renin is subsequently broken down by the body to an octapeptide known as angiotensin II. Antiotensin II is known to be a potent pressor substance, i.e., a substance that is capable of inducing a significant increase in blood pressure, and is believed to act by causing the constriction of blood vessels and the release of the sodium-retaining hormone aldosterone from the adrenal gland. Thus, the renin-angiotensinogen system has been implicated as a causative factor in certain forms of hypertension and congestive heart failure.

One means of alleviating the adverse effects of the functioning of the renin-angiotensinogen system is the administration of a substance capable of inhibiting the angiotensinogen-cleaving action of renin. A number of such substances are known, including antirenin antibodies, pepstatin and naturally-occurring phospholipid compounds.

Dellaria et al. [Tetrahedron Lett. 2337 (1986)] describes the synthesis of several phosphonate esters as antihypertensive agents.

European Patent Application 249,445A published Dec. 16, 1987 claims a series of phosphonate antihypertensive agents which act as enzyme inhibitors.

SUMMARY OF THE INVENTION

It has now been found that certain phosphorous containing polypeptides are useful as renin-inhibiting agents and have application in the treatment of hypertension and congestive heart failure.

This series of novel compounds consists of peptides of the formula

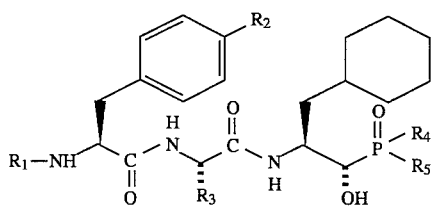

and a pharmaceutically acceptable salt thereof, wherein $R_1$ is $(CH_3O)_2PO-$, $(CH_2)_3O_2PO-$ or X—Y—, where X is morpholino, N-methylpiperazino, piperidino, pyrrolidin-1-yl, pyrrolyl, 3-oxopyrrolidin-1-yl, imidazolyl, cis-4-hydroxycyclohexyl, trans-4-hydroxycyclohexyl, acetylalkyl having three to six carbon atoms, alkyl having one to three carbon atoms, 4-oxopiperidino, 4-oxocyclohexyl, alkoxy having one to five carbon atoms or 4-hydroxypiperidino and Y is $CH_2C=O$ or $C=O$; $R_2$ is hydrogen or methoxy; $R_3$ is alkyl having one to four carbon atoms, methoxyalkyl said alkyl having one to three carbon atoms, methylthioalkyl said alkyl having one to three carbon atoms, hydroxymethyl, imidazol-4-ylmethyl, methylsulfonylmethyl, methylsulfinylmethyl or carbamylethyl; $R_4$ and $R_5$ when considered separately are each alkyl having one to three carbon atoms, benzyloxy, alkoxy having one to four carbon atoms, dimethylamino or hydroxy; and $R_4$ and $R_5$ when taken together are alkylene having four to six carbon atoms, alkylenedioxy having three to four carbon atoms or mono- or dimethylalkylenedioxy having four to six carbon atoms.

A preferred group of compounds are those where $R_1$ is X—Y— where X is morpholino, Y is $C=O$, $R_2$ is hydrogen and $R_3$ is methylthioalkyl said alkyl having one to three carbon atoms. Especially preferred within this group are compounds where $R_3$ is methylthiomethyl and $R_4$ is methoxy and $R_5$ is isopropoxy, where $R_4$ and $R_5$ together are butylene and where $R_4$ and $R_5$ together are propylenedioxy.

A second group of preferred compounds are those where $R_1$ is X—Y— where X is 4-oxopiperidino, Y is $C=O$, $R_2$ is hydrogen and $R_3$ is methylthioalkyl said alkyl having one to three carbon atoms. Especially preferred within this group are compounds where $R_3$ is methylthiomethyl and $R_4$ and $R_5$ are each methoxy, where $R_4$ and $R_5$ together are propylenedioxy and where $R_4$ and $R_5$ together are pentylene.

A third group of preferred compounds are those where $R_1$ is X—Y— where X is morpholino, Y is $C=O$, $R_2$ is hydrogen and $R_3$ is alkyl having one to four carbon atoms. Especially preferred within this group is the compound where $R_3$ is n-butyl and $R_4$ and $R_5$ are each methoxy.

The present invention also includes a method for treating hypertension in a mammal which comprises administering to said mammal an antihypertensive effective amount of the compounds of the present invention and a pharmaceutical composition comprised of the compounds of the present invention in unit dosage form and a carrier.

As previously indicated, the present invention embraces pharmaceutically acceptable salts of the biologically active compounds. Such salts are those which are non-toxic at the dosages administered. Since compounds of the invention may contain both basic and acidic groups, both acid addition and alkali addition salts are possible. Pharmaceutically acceptable acid addition salts include e.g., the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts. Pharmaceutically acceptable alkali addition salts include e.g., the sodium, potassium, calcium and magnesium salts. Conventional methods of forming acid addition and alkali addition salts may be employed.

In the interest of brevity, the commonly accepted abbreviated name of the individual amino acids have been employed where possible. For example, the following abbreviations have been used:

Phe—phenylalanine
SMeCys—S-methyl-L-cysteine
OMeHse—O-methyl-homoserine
Etg—L-ethylglycine
Nva—L-norvaline
OMeTyr—O -methyl-L-tyrosine HACPP—(1-hydroxy-2-amino-3-cyclohexylpropyl)phosphoryl

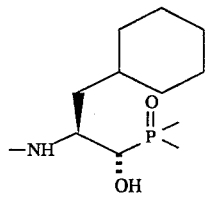

HBT—hydroxybenzotriazole
DEC—dimethylaminopropyl ethyl carbodiimide
BOC—t-butoxycarbonyl
OBN—o-benzyl, etc.

All the natural amino acid contained in the structures of the instantly claimed compounds are of the L configuration, the naturally occurring configuration, unless otherwise noted.

DETAILED DESCRIPTION OF THE INVENTION

The compounds of this invention exhibit antihypertensive activity in vivo in mammals, including humans. At least a substantial portion of this activity results from their ability to inhibit the cleavage of angiotensinogen by renin. Although we do not wish to be limited by the following theory of mechanism, it is likely that the mechanism of the renin-inhibiting activity of the compounds of the invention is their selective binding (as compared to angiotensinogen) to renin. The compounds of the invention exhibit an enzyme-inhibiting activity that is selective for renin as against other beneficial enzymes such as cathepsin D. Because of their low molecular weights they exhibit favorable solubility characteristics in aqueous media, thus making oral administration feasible, and can be synthesized at a commercially realistic cost. The compounds of the present invention are also useful against congestive heart failure.

The compounds of the invention can be prepared by methods familiar to those skilled in the art. The basic sub-unit of the preferred chemical synthesis is the acylation of the unprotected alpha-amino group of an amino acid residue with an amino acid having an activated (for acylation purposes) carboxylic function and a suitable protecting group bonded to its own alpha-nitrogen to form a peptide bond between the two amino acid residues, followed by the removal of said protecting group. This synthesis sub-unit of coupling-deblocking is performed repeatedly to build up the polypeptide, starting from the C-terminal end of the molecular structure and working to the N-terminal end.

Alternatively, a preformed dipeptide portion can be coupled with a single amino acid using the polypeptide coupling techniques or the preformed tripeptide can be acylated with $R_1$ using known acylation methods. The amino acids utilized to synthesize the compounds of the present invention are commercially available (as free acids, salts or esters, etc.) in both alpha-amino protected and alpha-amino unprotected forms.

The amides or esters, when subjected to hydrogen chloride in dioxane, lose the t-butoxycarbonyl protecting group from the amino moiety. Acylation of the resulting amino esters or amides are carried out using 1-hydroxybenzotriazole and a carbodiimide. Removal of the blocking group on imidazole with acetic acid-water gives the final product.

The activity of the compounds of the present invention as inhibitors of the angiotensinogen-cleaving activity of renin can be determined by studying (1) their ability to inhibit the angiotensinogen-cleaving activity of renin in vitro and (2) their ability to antagonize the exogenous renin-induced pressor response in vivo.

The compounds of the present invention can be administered as antihypertensive agents by either the oral or parenteral routes of administration, with the former being preferred for reasons of patient convenience and comfort. In general, these antihypertensive compounds are normally administered orally in dosages ranging from about 0.5 mg to about 50 mg per kg of body weight per day and 0.1 mg to about 5 mg per kg of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The following examples illustrate the invention but are not to be construed as limiting the same.

All NMR data are partial. When two diastereomers are formed, NMR data are given for the major only.

EXAMPLE 1

Morpholinocarbonyl-PheNle-HACPP(OCH$_3$)$_2$ ($R_1$= morpholinocarbonyl; $R_2$= H; $R_3$= n-C$_4$H$_9$; and $R_4$, $R_5$= OCH$_3$)

A. BocHACPP(OCH₃)₂

A solution containing 100 mg Boc-L-cyclohexylalanal, 86 mg of dimethyl phosphite and 183 mg of potassium fluoride monohydrate in 0.25 ml of dimethylformamide was stirred at room temperature under a nitrogen atmosphere for 20 hours. The reaction mixture was diluted with 15 ml of methylene chloride and was washed with water (3×5 ml). The organic phase was separated, dried over magnesium sulfate and concentrated. The residue was chromatographed (ethyl acetate-hexane, 3:1, v:v) to afford 120 mg of product as a 3:1 mixture of hydroxyl-group epimers.

NMR (300 Hz, CDCl₃)delta 1.44 (s, 9H), 3.78 (d, J=10 Hz, 3H), 3.81 (d, J=10 Hz, 3H) and 3.94 (m, 2H).

B. HACPP (OCH₃)₂.HCl

A solution of the product of Example 1A (100 mg) in 2 ml of 4N hydrogen chloride in dioxane was stirred at room temperature for 45 minutes. The solution was concentrated in vacuo to give 90 mg of the desired hydrochloride.

NMR (300 MHz, DMSO-d₆)delta 3.74 (d, J=11 Hz, 3H) and 3.78 (d, J=11Hz, 3H).

C. Morpholinocarbonyl-Phe

To a solution of 166 g of phenylalanine in 500 ml of 2N sodium hydroxide and 2 liters of dioxane at 0° C. was added 150 g of morpholinocarbonyl chloride over a 5 minute period. Sodium hydroxide was added occasionally to maintain the pH at about 11. After 4 hours the mixture was concentrated and washed with methylene chloride (3×500 ml). The aqueous layer was separated, acidified with 12N hydrochloric acid and extracted with methylene chloride (4×500 ml). The extracts were combined, dried over magnesium sulfate and concentrated to afford 238 g of the desired product.

NMR (300 MHz, DMSO-d₆)delta 3.26 (m, 4H), 3.52 (m, 4H), 4.25 (m, 1H) and 6.75 (d, J=8 Hz, 1H).

D. Morpholinocarbonyl-PheNleO-Bn

To a solution of 3.0 g of the product of Example 1C and 2.9 g of L-norleucine benzylester in 50 ml of methylene chloride was added 1.6 ml of triethylamine, 2.19 g of HBT and 2.3 g of DEC, and the resulting solution stirred at room temperature for 16 hours. The mixture was diluted with 400 ml of ethyl acetate and washed with 0.1N hydrochloric acid (1×40 ml), a saturated sodium bicarbonate solution (2×40 ml) and a saturated brine solution (1×40 ml). The organic phase was separated, dried over magnesium sulfate and concentrated. The residue was chromatographed (methanol-methylene chloride, 1:19, v:v) to afford 4.23 g of desired product.

NMR (300 MHz, CDCl₃)delta 0.80 (t, J=7 Hz, 3H), 4.49 (m, 1H), 4.59 (m, 1H) and 5.03 (s, 2H).

E. Morpholinocarbonyl-PheNle

A mixture of 4.32 g of the product of Example 1D and 1.05 g of 10% palladium-on-charcoal in 200 ml of methanol was shaken in a hydrogen atmosphere at a pressure of 50 psi for 4 hours. The mixture was filtered and concentrated to give 3.78 g of crude acid.

NMR (300 MHz, DMSO-d₆)delta 0.88 (br, 3H), 4.15 (m, 1H) and 4.33 (m, 1H).

F. Morpholinocarbonyl-PheNle-HACPP (OCH₃)₂

To a solution of 120 mg of the product of Example 1E and 84 mg of the product of Example 1B in 2 ml of dry methylene chloride was added 31 mg of dry triethylamine, 70 mg of HBT and 59 mg of DEC. After stirring overnight at room temperature, the mixture was diluted with 20 ml of methylene chloride and was washed with 0.1N hydrochloric acid (1×10 ml) and 0.1N sodium hydroxide solution (1×10 ml). The organic layer was separated, dried over magnesium sulfate and concentrated in vacuo. The residue was chromatographed (methanol-methylene chloride, 7.5:92.5, v:v) to afford 90 mg of desired product as a 3:1 mixture of hydroxyl-group epimers.

NMR (300 MHz, CDCl₃)delta 3.75 (d, J=10 Hz, 3H), 3.78 (d, J=10 Hz, 3H) , 3.99 (m, 1H), 4.25 (m, 1H), 4.35 (m, 1H) and 4.61 (m, 1H).

EXAMPLES 2–9

Employing the procedures of Example 1 and starting with the appropriate dialkyl phosphite and S-methyl-L-cysteine in place of L-norleucine the following compounds were prepared:

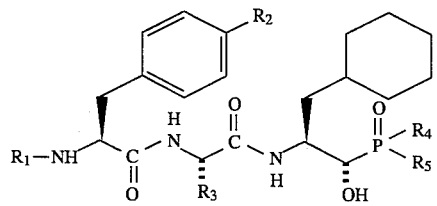

| $R_1$ | $R_2$ | $R_3$ | $R_4$ | $R_5$ | NMR(300MHz)delta |
|---|---|---|---|---|---|
| ⌒O⌒N—C(=O)— | H | $CH_3SCH_2$ | $OCH_3$ | $OCH_3$ | CDCl₃: 2.10(s, 3H), 3.76(m, 6H), 4.00(m, 1H), 4.32(m, 1H), 4.55 (m, 2H). |
| ⌒O⌒N—C(=O)— | H | $CH_3SCH_2$ | $OC_2H_5$ | $OC_2H_5$ | CDCl₃: 2.06(s, 3H), 3.84(dd, J=3, 13Hz, 1H), 4.10(m, 4H), 4.27(m, 1H), 4.46(m, 1H), 4.78 (m, 1H). |

-continued

| $R_1$ | $R_2$ | $R_3$ | $R_4$ | $R_5$ | NMR(300MHz)delta |
|---|---|---|---|---|---|
| 3-oxomorpholin-4-yl | H | $CH_3SCH_2$ | $O$-$i$-$C_3H_7$ | $O$-$i$-$C_3H_7$ | $CDCl_3$: 1.33(2xd, 12H), 2.02(s, 3H), 4.46(m, 2H), 4.72(m, 2H). |
| 3-oxomorpholin-4-yl | H | $CH_3SCH_2$ | $OCH_3$ | $O$-$i$-$C_3H_7$ | $CDCl_3$: 2.38(d, J=6Hz, 6H), 1.18(brs, 3H), 3.95 (m, 1H), 4.53(m, 2H), 4.78(m, 1H). |
| 3-oxomorpholin-4-yl | H | $CH_3SCH_2$ | $OCH_2C_6H_5$ | $OCH_2C_6H_5$ | $CDCl_3$: 4.01(dd, J=4Hz, 1H), 4.27(m, 2H), 4.52 (m, 1H), 5.50(m, 1H). |
| 3-oxomorpholin-4-yl | H | $CH_3SCH_2$ | $OCH_2C_6H_5$ | $OCH_3$ | $CDCl_3$: 2.13(s, 3H), 3.73 d, J=10Hz, 3H), 4.48(m, 2H), 5.16(m, 2H). |
| 3-oxomorpholin-4-yl | H | $CH_3SCH_2$ | ← $-OC(CH_3)_2(CH_2)_2-O-$ → | | $CDCl_3$: 1.44(s, 3H), 1.49 (s, 3H), 2.09(s, 3H), 3.89(m, 1H), 4.18(m, 1H), 4.40(m, 2H), 4.52 (m, 2H). |
| 3-oxomorpholin-4-yl | H | $CH_3(CH_2)_3-$ | $OCH_2C_6H_5$ | $OCH_2C_6H_5$ | $CDCl_3$: 4.01(dd, J=4, 10Hz, 1H), 4.27(m, 2H), 4.52(m, 1H), 5.50(m, 4H). |

EXAMPLE 10

3-Oxopyrrolidin-1-ylcarbonyl-PheSMeCysHACPP(OCH$_3$)$_2$ ($R_1$=3-oxopyrrolidin-1-ylcarbonyl; $R_2$= H; $R_3$= $CH_3SCH_2$; and $R_4$, $R_5$= $OCH_3$)

Following the procedure of Example 1, but substituting 3-oxopyrrolidin-1-ylcarbonyl for morpholinocarbonyl and S-methyl-L-cysteine for L-norleucine, the title compound was prepared.

NMR (300 MHz, CDCl$_3$)delta 2.14 (s, 3H), 3.78 (d, J=11 Hz, 3H), 3.81 (d, J=10 Hz, 3H), 4.20 (m, 1H), 4.43 (m, 1H), 4.54 (m, 1H) and 4.80 (m, 1H).

EXAMPLE 11

Imidazol-4-ylcarbonyl-PheSMeCys-HACPP(OCH$_3$)$_2$ ($R_1$= imidazol-4-ylcarbonyl; $R_2$= H; $R_3$= $CH_3SCH_2$; and $R_4$,$R_5$=$OCH_3$)

A. BocSMeCys-HACPP(OCH$_3$)$_2$

Employing the procedure in Example 1D, 1.2 g of Boc-S-methyl-L-cysteine was coupled with 1.0 g of HACPP(OCH$_3$)$_2$.HCl using the DEC procedure. The crude product was chromatographed (methanol-methylene chloride, 1:19, v:v) to afford 1.2 g of product as a 3:1 mixture of hydroxyl epimers.

NMR (300 MHz, CDCl$_3$)delta 1.44 (s, 9H), 2.15 (s, 3H), 3.78 (d, J=10 Hz, 3H) and 3.89 (d, J=10 Hz, 3H).

B. SMeCys-HACPP (OCH$_3$)$_2$.HCl

The product of Example 11A (1.2 g) was treated with 4N hydrogen chloride in dioxane at room temperature for 2 hours to afford 1.1 g of the desired product.

NMR (300 MHz, DMSO-d$_6$)delta 2.14 (s, 3H), 3.63 (d, J=10 Hz, 3H) and 3.68 (d, J=10 Hz, 3H).

C. BocPheSMeCys-HACPP (OCH$_3$)$_2$

Boc phenylalanine (1.14 g) was coupled with 1.0 g of the product of Example 11B using the DEC procedure of Example 1D. The crude product was chromatographed (methanol-methylene chloride, 1:19, v:v) to afford 1.04 g of pure material.

NMR (300 MHz, CDCl$_3$)delta 1.37 (s, 9H), 2.10 (s, 3H), 3.78 (d, J=12 Hz, 6H), 3.93 (dd, J=4, 11Hz, 1H), 4.18 (m, 1H), 4.35 (m, 1H) and 4.52 (m, 1H).

D. PheSMeCys-HACPP (OCH$_3$)$_2$.HCl

A solution of 1.04 g of the product of Example 11C was stirred in 15 ml of 4N hydrogen chloride in dioxane for 30 minutes at room temperature. The reaction mixture was concentrated and the residue dried under high vacuum to give 1.01 g of crude product.

NMR (300 MHz, DMSO-d$_6$)delta 2.06 (s, 3H), 3.80 (m,

1H), 4.04 (m, 2H) and 4.50 (m, 1H).

E. Imidazol-4-ylcarbonyl-PheSMeCys-HACPP (OCH₃)₂

Imidazole-4-carboxylic acid (34 mg) was coupled with 166 mg of the product of Example 11D using the standard DEC procedure in dimethylformamide as described in Example 1D. The crude material was chromatographed (methanol-methylene chloride, 1:9, v:v) to give 79 mg of product as a mixture of hydroxyl epimers.

NMR (300 MHz, CDCl₃)delta 2.06 (s, 3H), 3.77 (d, J=10 Hz, 3H), 3.85 (d, J=10 Hz, 3H), 3.97 (br d, J=13 Hz, 1H), 4.36 (m, 1H), 4.52 (m, 1H), 4.60 (m, 1H) and 4.80 (m, 1H).

EXAMPLES 12–16

Employing the procedure of Example 11E and starting with the appropriate acid and the product of Example 11D, the following compounds were prepared:

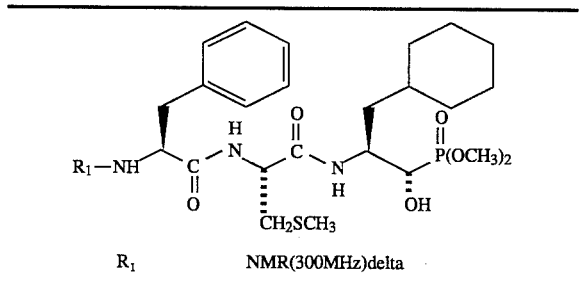

| $R_1$ | NMR(300MHz)delta |
|---|---|
| 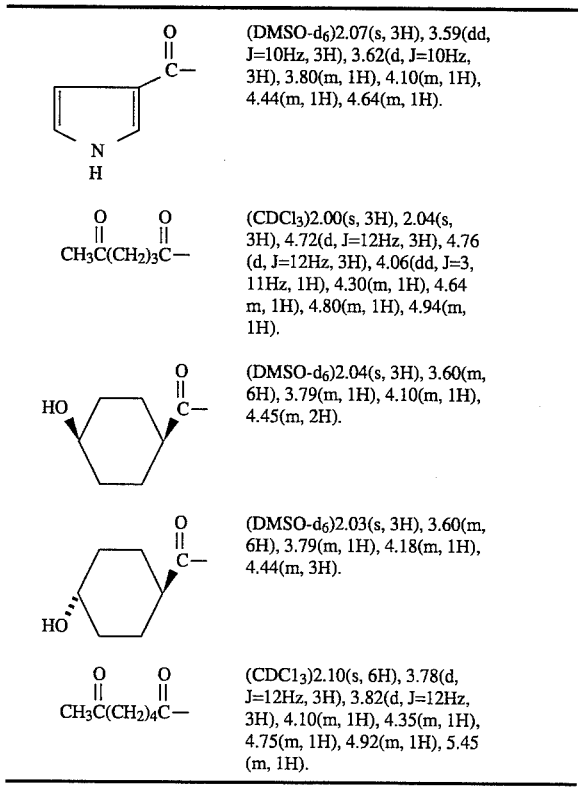 | (DMSO-d₆)2.07(s, 3H), 3.59(dd, J=10Hz, 3H), 3.62(d, J=10Hz, 3H), 3.80(m, 1H), 4.10(m, 1H), 4.44(m, 1H), 4.64(m, 1H). |
| | (CDCl₃)2.00(s, 3H), 2.04(s, 3H), 4.72(d, J=12Hz, 3H), 4.76 (d, J=12Hz, 3H), 4.06(dd, J=3, 11Hz, 1H), 4.30(m, 1H), 4.64 m, 1H), 4.80(m, 1H), 4.94(m, 1H). |
| | (DMSO-d₆)2.04(s, 3H), 3.60(m, 6H), 3.79(m, 1H), 4.10(m, 1H), 4.45(m, 2H). |
| | (DMSO-d₆)2.03(s, 3H), 3.60(m, 6H), 3.79(m, 1H), 4.18(m, 1H), 4.44(m, 3H). |
| | (CDCl₃)2.10(s, 6H), 3.78(d, J=12Hz, 3H), 3.82(d, J=12Hz, 3H), 4.10(m, 1H), 4.35(m, 1H), 4.75(m, 1H), 4.92(m, 1H), 5.45 (m, 1H). |

EXAMPLES 17–18

Using the procedure of Example 11 and substituting HACPP(OC₂H₅)₂ for HACPP(OCH₃)₂ and starting with the requisite acid, the following analogs were prepared:

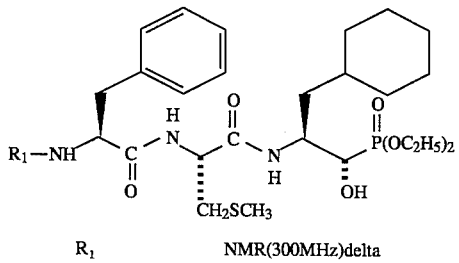

| $R_1$ | NMR(300MHz)delta |
|---|---|
| 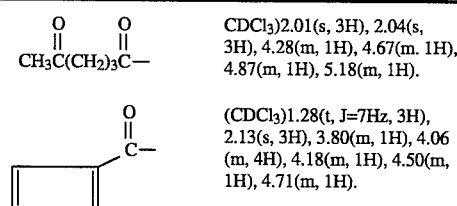 | CDCl₃)2.01(s, 3H), 2.04(s, 3H), 4.28(m, 1H), 4.67(m. 1H), 4.87(m, 1H), 5.18(m, 1H). |
| | (CDCl₃)1.28(t, J=7Hz, 3H), 2.13(s, 3H), 3.80(m, 1H), 4.06 (m, 4H), 4.18(m, 1H), 4.50(m, 1H), 4.71(m, 1H). |

EXAMPLE 19

Morpholinocarbonyl-PheSer-HACPP (OCH₃)₂
($R_1$=morpholinocarbonyl; $R_2$= H; $R_3$=HOCH₂—; and $R_4$, $R_5$=OCH₃)

A. Boc Ser-HACPP (OCH₃)₂

Using the DEC coupling procedure of Example 1D 210 mg of BocSerOH was reacted with 278 mg of HACPP (OCH₃)₂. HCl to give, after chromatographing (methanol-methylene chloride, 1:19, v:v), 165 mg of the desired product as the less polar product and 41 mg of the hydroxyl epimer.

NMR(300 MHz, CDCl₃)delta 1.41 (s, 9H), 3.70 (d, J=10 Hz, 3H) and 3.82 (d, J=10 Hz, 3H).

B. Ser-HACPP (OCH₃)₂.HCl

The product of Example 19A (159 mg) was deprotected using hydrogen chloride according to the procedure of Example 1B to give 79 mg of the product.

NMR(300 MHz, DMSO-d₆)delta 3.61 (d, J=10 Hz, 3H) and 3.65 (d, J=10 Hz, 3H).

C. Morpholinocarbonyl-PheSer-HACPP (OCH₃)₂

Morpholinocarbonyl-Phe (61 mg) was coupled with mg of Ser-HACPP(OCH₃)₂.HCl using the DEC procedure of Example 1D to afford, after chromatographing (methanol-methylene chloride, 1:9, v:v), 47 mg of the desired product.

NMR(300 MHz, CDCl₃)delta 3.62 (d, J=10 Hz, 3H), 3.83 (d, J=10 Hz, 3H) and 4.20 (m, 3H).

EXAMPLE 20

Morpholinocarbonyl-PheHis-HACPP(OCH₃)₂ ($R_1$= morpholinocarbonyl; $R_2$= H; $R_3$= imidazol-4-ylmethyl; and $R_4$, $R_5$= OCH₃

The titled compound was prepared according to the procedure of Example 19, substituting BocHis for BocSer.

NMR(300 MHz, acetone-d₆)delta 3.72 (d, J=13 Hz, H), 3.76 (d, J=13 Hz, 3H), 3.87 (dd, J=5, 10 Hz, 1H), 4.27 (m, 1H), 4.38 (m, 1H) and 4.54 (m, 1H).

EXAMPLE 21

4-Oxopiperidinocarbonyl -PheSMeCys-HACPP (OCH$_3$ )$_2$ (R$_1$=4-oxopiperidinocarbonyl; R$_2$= H; R$_3$= CH$_2$SCH$_3$; and R$_4$, R$_5$=OCH$_3$)

A. 4-Oxopiperidinocarbonyl-PheOBn ethylene glycol ketal

To a solution of PheOBn-isocyanate (450 mg) in 20 ml of methylene chloride at 0° C. was added 215 µl of the ethylene glycol ketal of 4-oxopiperidine, and the resulting reaction mixture allowed to stir overnight at room temperature. The reaction mixture was diluted with ethyl acetate (200 ml) and washed with 20 ml of a 0.1N sodium hydroxide solution. The organic phase was dried over magnesium sulfate and concentrated in vacuo to give, after chromatographing (methanol-methylene chloride, 1:19, v:v), 490 mg of pure product.

NMR(300 MHz, CDCl$_3$)delta 3.94 (s, 4H), 3.84 (m, 2H) and 5.12 (AB, 2H).

B. 4-Oxopiperidinocarbonyl-PheOH ethylene glycol ketal

A mixture of 480 mg of the benzyl ester product from Example 21A and 500 mg of 10% palladium-on-charcoal in 30 ml of methanol was shaken in a hydrogen atmosphere at an initial pressure of 50 psi for 3 hours. The catalyst was filtered and the filtrate concentrated in vacuo to give 400 mg of product.

NMR(300 MHz, DMSO-d$_6$)delta 3.87 (s, 4H) and 4.18 (m, 2H).

C. 4-Oxopiperidinocarbonyl-PheSMeCys-HACP-P(OCH$_3$)$_2$ ethylene glycol ketal

The product of Example 21B (251 mg) was coupled with 200 mg of the product of Example 11B using the DEC procedure of Example 1D. The crude product was chromatographed (methanol-methylene chloride, 1: 19, v: v) to afford 147 mg of the desired material as a 3:1 mixture of hydroxyl epimers.

NMR(300 MHz, CDCl$_3$)delta 2.14 (s, 3H), 3.82 (d, J=10 Hz, 3H), 3.83 (d, J=10 Hz, 3H) and 3.96 (s, 4H).

D. 4-Oxopiperidinocarbonyl-PheSMeCys-HACPP (OCH$_3$)$_2$

A solution of the ketal of Example 21C in 5 ml of tetrahydrofuran and 5 ml of 10% hydrochloric acid was stirred at room temperature for 6 hours. The mixture was treated with 200 ml of ethyl acetate and the organic layer washed with a saturated sodium bicarbonate solution (2×20 ml). The organic phase was dried over magnesium sulfate and concentrated in vacuo. The residue, after chromatographing (methanol-methylene chloride, 1:19, v:v), afforded 100 mg of the desired material as a 3:1 mixture of hydroxyl epimers.

NMR(300 MHz, CDCl$_3$)delta 2.10 (s, 3H), 3.76 (d, J=11 Hz, 3H), 3.79 (d, J=11 Hz, 3H), 4.20 (m, 1H), 4.5 (m, 3H) and 4.72 (m, 1H).

EXAMPLES 22–27

Employing the procedures of Example 21 and substituting the appropriate Boc-protected amino acid for Boc-SMeCys, the following compounds were prepared:

| R$_3$ | NMR(300MHz)delta |
|---|---|
| H$_2$NC(O)(CH$_2$)$_2$— | (CDCl$_3$)3.73(d, J=13Hz, 3H), 3.77(d, J=12Hz, 3H), 3.92(m, 1H), 4.35(m, 2H), 4.54(m, 1H). |
| CH$_3$(CH$_2$)$_2$— | (CDCl$_3$)3.80(m, 6H), 4.08(m, H), 4.40(m, 3H), 4.78(m, 1H). |
| (imidazolyl)CH$_2$— | (DMSO-d$_6$)3.64(d, J=11Hz, 3H), 3.66(d, J=11Hz, 3H), 3.78(m, 1H), 4.12(m, 1H), 4.32(m, 1H), 4.45(m, 1H). |
| CH$_3$— | (CDCl$_3$)1.36(d, J=8Hz, 3H), 3.73(d, J=13Hz, 3H), 3.76(d, J=12Hz, 3H), 3.97(dd, J=3, 12 Hz, 1H), 4.20(m, 1H), 4.42 (m, 1H), 4.61 (m, 1H). |
| CH$_3$O(CH$_2$)$_2$— | (CDCl$_3$)3.22(s, 3H), 3.78(d, J=12Hz, 3H), 3.80(d, J=12Hz, 3H), 3.94(dd, J=3, 11Hz, 1H), 4.28(m, 1H), 4.39(m, 1H), 4.52 (m, 1H). |
| CH$_3$CH$_2$— | (CDCl$_3$)3.79(d, J=12Hz, 3H), 3.82(d, J=12Hz, 3H), 4.05(dd, J=4, 12Hz, 1H), 4.30(m, 1H), 4.38(m, 1H), 4.70(m, 1H). |

EXAMPLES 28–32

Using the procedures of Example 21 and substituting the requisite phenylalanine derivative, the following compounds were prepared:

| R$_1$ | NMR(300MHz)delta |
|---|---|
| CH$_3$C(O)— | (CDCl$_3$)0.97(s, 3H), 2.11(br.s, 3H), 3.75(d, J=10Hz, 3H), 3.79 (d, J=10Hz, 3H), 3.98(dd, J=2, 12Hz, 1H), 4.20(m, 1H), 4.52 (m, 1H), 4.68(m, 1H) |
| 4-hydroxycyclohexyl-NC(O)— | (CDCl$_3$)2.12(s, 3H), 3.81(d, J= 12Hz, 3H), 3.83(d, J=12Hz, 3H), 3.95(dd, J=2, 12Hz, 1H), 4.28(m, 1H), 4.38(m, 1H), 4.58 (m, 1H). |

-continued

| $R_1$ | NMR(300MHz)delta |
|---|---|
| cyclohexanone-C(=O)— | (CDCl$_3$)2.12(s, 3H), 3.79(d, J= 10Hz, 3H), 3.83(d, J=10Hz, 3H), 4.12(m, 1H), 4.40(m, 1H), 4.90(m, 1H), 5.08(m, 1H). |
| CH$_3$N(piperazine)N—C(=O)— | (CDCl$_3$)2.12(s, 3H), 3.79(d, J= 11Hz, 3H), 3.81(d, J=11Hz, 3H), 3.95(m, 1H), 4.28(m, 1H), 4.39(m, 1H), 4.57(m, 1H). |
| (CH$_3$O)$_2$P(=O)— | (CDCl$_3$)2.09(s, 3H), 3.48(d, J= 12Hz, 3H), 3.52(d, J=12Hz, 3H), 3.76(d, J=12Hz, 6H), 3.98(dd, J=3, 11Hz, 1H), 4.03(m, 1H), 4.23(m, 1H), 4.68(m, 1H). |

Structure: R$_1$—NH—CH(CH$_2$Ph)—C(=O)—NH—CH(CH$_2$SCH$_3$)—C(=O)—NH—CH(CH$_2$-cyclohexyl)—CH(OH)—P(=O)(OCH$_3$)$_2$

EXAMPLE 33

3-Oxopyrrolidinoacetyl-PheSMeCys-HACPP (OCH$_3$)$_2$ (R$_1$=3-oxopyrrolidinoacetyl; R$_2$= H; R$_3$=CH$_2$SCH$_3$; and R$_4$, R$_5$=OCH$_3$)

A. Chloroacetyl-PheOBn

To a stirred solution of 2.0 g of phenylalanine benzyl ester hydrochloride and 2.0 ml of triethylamine in 40 ml of methylene chloride at 0° C. was added dropwise a solution of 0.53 ml of chloroacetyl chloride in 10 ml of methylene chloride, and the solution allowed to stir at room temperature for 3 hours. The mixture was poured into 200 ml of water and extracted with ethyl acetate (2×200 ml). The extracts were combined, washed with 0.1N hydrochloric acid (2×40 ml) and 0.1N sodium hydroxide solution (2×40 ml) and dried over magnesium sulfate. The solvent was removed in vacuo and the residue triturated with hexane to give 1.97 g of product.

NMR(300 MHz, CDCl$_3$)delta 3.16 (d, J=6 Hz, 2H), 4.03 (s, 2H) and 4.91 (m, 1H).

B. 3-Hydroxypyrrolidinoacetyl-PheOBn

A mixture of 510 mg of the product of Example 33A and 300 mg of 3-hydroxypyrrolidine in 15 ml of tetrahydrofuran was heated to 55° C. for 16 hours. The mixture was poured into 100 ml of water and extracted with ethyl acetate (2×100 ml). The combined extracts were washed with water, dried over magnesium sulfate and concentrated. The crude product was chromatographed (methanol-methylene chloride, 1:9, v:v) to give 500 mg of pure product as a mixture of hydroxyl epimers.

C. 3-Oxopyrrolidinoacetyl-PheOBn

To a solution of 0.2 ml of dimethylsulfoxide in 3 ml of methylene chloride at −60° C. was added 0.14 ml of oxalyl chloride and the resulting solution was stirred for 20 minutes at −60° C. A solution of 0.49 g of the product of Example 33B in 10 ml of methylene chloride was added dropwise and the solution allowed to warm to −30° C. The mixture was cooled to −78° C. and 0.89 ml of triethylamine was added. The reaction mixture was allowed to warm to room temperature for 1 hour, and was then poured into 100 ml of water. The quench was extracted with ethyl acetate (2×200 ml) and the extracts combined, washed with a saturated sodium bicarbonate solution and dried over magnesium sulfate. The crude product was chromatographed (methanol-methylene chloride, 1:9, v:v) to give 460 mg of pure material.

NMR(300 MHz, CDCl$_3$)delta 2.34 (t, J=7 Hz, 2H), 4.92 (m, 1H) and 5.17 (AB, 2H).

D. 3-Oxopyrrolidinoacetyl-Phe

A mixture of 460 mg of the product of Example 33C and 460 mg of 10% palladium-on-charcoal was shaken in a hydrogen atmosphere at an initial pressure of 50 psi. The spent catalyst was filtered and the filtrate concentrated to give 340 mg of the desired product.

NMR(300 MHz, CDCl$_3$)delta 2.30 (t, J=6 Hz, 2H), 4.42 (m, 1H) and 7.20 (m, 5H).

E. 3-Oxopyrrolidinoacetyl-PheSMeCys-HACPP (OCH$_3$)$_2$

The product of Example 33D (100 mg) was coupled with 125 mg of the product of Example 11B using the DEC procedure of Example 1D. The crude product was chromatographed (methanol-methylene chloride, 1:19, v:v) to give 86 mg of product as a mixture of hydroxy epimers.

NMR(300 MHz, CDCl$_3$)delta 2.14 (s, 3H), 3.78 (d, J=11 Hz, 3H), 3.79 (d, J=11 Hz, 3H), 4.00 (m, 1H), 4.17 (m, 1H) and 4.57 (m, 2H).

EXAMPLES 34–36

The procedure of Example 33 was employed using the appropriate amine in place of 3-hydroxypyrrolidine to give the following products:

Structure: R$_1$—NH—CH(CH$_2$Ph)—C(=O)—NH—CH(CH$_2$SCH$_3$)—C(=O)—NH—CH(CH$_2$-cyclohexyl)—CH(OH)—P(=O)(OCH$_3$)$_2$

| $R_1$ | NMR(300MHz)delta |
|---|---|
| HO-cyclohexyl-NCH$_2$C(=O)— | (CDCl$_3$)2.11(s, 3H), 3.78(d, J= 11Hz, 3H), 3.80(d, J=11Hz, 3H), 3.98(m, 1H), 4.18(m, 1H), 4.57(m, 2H). |
| O=cyclohexyl-NCH$_2$C(=O)— | (CDCl$_3$)2.14(s, 3H), 3.78(d, J= 12Hz, 6H), 4.00(m, 1H), 4.19 (m, 1H), 4.60(m, 2H). |

-continued

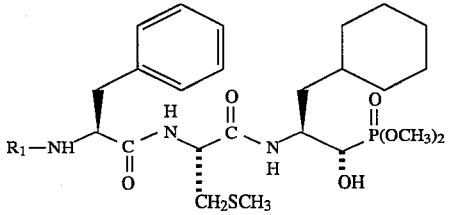

| $R_1$ | NMR(300MHz)delta |
|---|---|
| 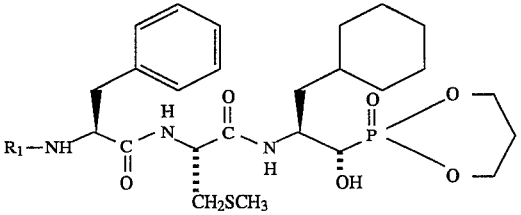 | (CDCl₃)2.12(s, 3H), 3.77(d, J= 11Hz, 3H), 3.78(d, J=11Hz, 3H), 3.98(m, 1H), 4.17(m, 1H), 4.57(m, 2H). |

EXAMPLE 37

4-Oxopiperidinocarbonyl-PheSMeCys-HACPP
(OCH₂CH₂CH₂O) (R₁=4-oxopiperidinocarbonyl;
R₂= H; R₃= CH₂SCH₃; and R₄, R₅
together=—OCH₂CH₂CH₂O—)

Employing the procedure of Example 21 but substituting HP(OCH₂CH₂CH₂O) for dimethylphosphite gave the titled compound.

NMR(300 MHz, CDCl₃)delta 2.09 (s, 3H), 4.10 (m, 2H), 4.37 (m, 2H), 4.46 (m, 1H), 4.60 (m, 1H) and 4.72 (m, 2H).

EXAMPLES 38–42

Employing the procedures of Examples 21/37 and substituting the requisite phenylalanine derivative for 4-oxopiperidinocarbonyl-Phe, the following analogs were prepared:

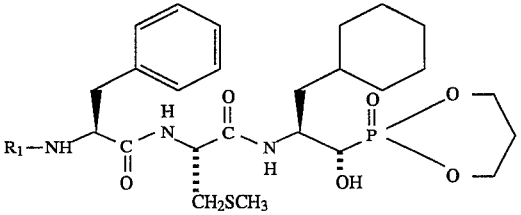

| $R_1$ | NMR(300MHz)delta |
|---|---|
| 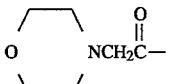 | (CDCl₃)1.97(s, 3H), 2.10(s, 3H), 4.29(m, 2H), 4.40(m, 2H), 4.68(m, 3H), 4.88 (m, 1H). |
| 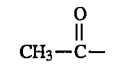 | (DMSO-d₆)2.06(s, 3H), 3.88(m, 1H), 4.10(m, 1H), 4.29(m, 3H), 4.42(m, 1H), 4.53(m, 2H). |
| 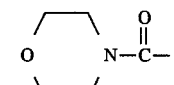 | (DMSO-d₆)2.04(s, 3H), 3.90(m, 1H), 4.09(m, 1H), 6.39(s, 1H), 6.86(s, 1H). |
| 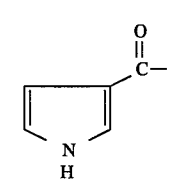 | (CDCl₃)2.12(s, 3H), 3.52(d, J= 12Hz, 6H), 4.12(m, 3H), 4.42 (m, 2H), 4.69(m, 3H). |
| 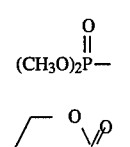 | (CDCl₃)2.15(br, 3H), 3.65 (m, 1H), 4.67(m, 2H), 4.76(m, 1H). |

EXAMPLES 43–45

Using the procedure of Example 21/37, but substituting the appropriate Boc-protected amino acid for Boc-SMeCys, the following compounds were prepared:

| $R_3$ | NMR(300MHz)delta |
|---|---|
| CH₃(CH₂)₂ | (CDCl₃)4.14(m, 2H), 4.43(m, 3H), 4.60(m, 1H), 4.76(m, 2H). |
| CH₃OCH₂— | (CDCl₃)3.38(s, 3H), 3.92(dd, J=4, 10Hz, 1H), 4.13(m, 2H), 4.82(m, 1H). |
| CH₃S(CH₂)₂— | (CDCl₃)2.04(s, 3H), 4.00(m, 1H), 4.11(m, 1H), 4.40(m, 3H), |

| $R_3$ | NMR(300MHz)delta |
|---|---|
| 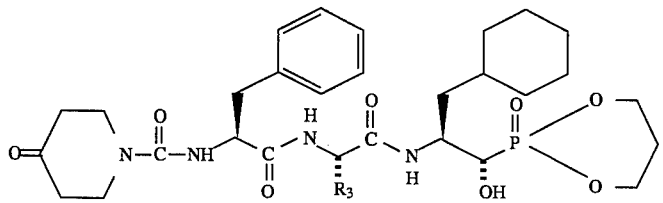 | 4.67(m, 3H). |

EXAMPLE 46

Morpholinocarbonyl-PheSMeCys-HACPP(O-EC$_3$H$_7$)$_2$
($R_1$= morpholinocarbonyl; $R_2$= H; $R_3$= CH$_3$SCH$_2$; and $R_4$, $R_5$=OCH$_2$CH$_2$CH$_3$)

The titled compound was prepared using the procedure of Example 19, substituting Boc-SMeCys for Boc-Ser and di-n-propylphosphite for dimethylphosphite.

NMR(300 MHz, CDCl$_3$)delta 2.13 (s, 3H), 3.58 (m, H), 3.82 (m, 1H) and 4.02 (m, 4H).

EXAMPLE 47

4-Oxopiperidinocarbonyl-PheSMeCys-HACPP (OCH$_3$) (O-nC$_3$H$_7$) ($R_1$=4-oxopiperidinocarbonyl; $R_2$= H; $R_3$=CH$_2$SCH$_3$; $R_4$=OCH$_3$; and $R_5$ = O-i-C$_3$H$_7$)

The titled compound was prepared employing the procedure of Example 21 but substituting methylisopropylphosphite for dimethylphosphite.

NMR(300 MHz, CDCl$_3$)delta 1.36 {d, J=6 Hz, 6H), 2.14 (s, 3H), 4.28 (m, 1H), 4.52 (m, 3H) and 4.75 (m, 1H).

EXAMPLE 48

4-Oxopiperidinocarbonyl-OMeTyrSMeCys-HACPP (OCH$_3$)$_2$ ($R_1$=4-oxopiperidinocarbonyl; $R_2$=CH$_3$O; $R_3$= CH$_3$SCH$_2$—; and $R_4$, $R_5$= OCH$_3$)

By substituting 0-methyl-L-tyrosine for L-phenylalanine and using the procedure of Example 21, the title compound was prepared.

NMR(300 MHz, CDCl$_3$)delta 2.12 (s, 3H), 3.76 (s, H), 4.98 (dd, J=4, 12 Hz, 1H), 4.26 (m, 1H) and 4.50 (m, 2H).

EXAMPLE 49

Morpholinocarbonyl-OMeTyrSMeCys-HACPP (OCH$_3$)$_2$ ($R_1$= morpholinocarbonyl; $R_2$=OCH$_3$; $R_3$=CH$_2$SCH$_3$; and $R_4$, $R_5$=OCH$_3$)

The titled compound was prepared by the procedures of Examples 21/48 by substituting morpholine for 4-oxopiperidine.

NMR(300 MHz, CDCl$_3$)delta 2.09 (s, 3H), 3.74 (s, 3H), 3.98 (m, 1H), 4.30 (m, 1H), 4.48 (m, 1H) and 4.55 (m, 1H).

EXAMPLE 50

4-Oxopiperidinocarbonyl-OMeTyrSMeCys-HACPP (OCH$_2$CH$_2$CH$_2$O) ($R_1$=4-oxopiperidinocarbonyl; $R_2$= CH$_3$O; $R_3$=CH$_2$SCH$_3$; and $R_4$, $R_5$ together=—O(CH$_2$)$_3$O—)

By replacing L-phenylalanine with OMe-L-tyrosine in the procedures of Examples 21/37, the titled compound was prepared.

NMR(300 MHz, CDCl$_3$)delta 2.12 (s, 3H), 3.78 (s, 3H), 4.13 (m, 1H), 4.26 (m, 1H), 4.39 (m, 3H), 4.58 (m, 1H) and 4.72 (m, 2H).

EXAMPLE 51

4-Oxopiperidinocarbonyl-PheSO$_2$MeCys-HACPP (OCH$_2$CH$_2$CH$_2$O) ($R_1$=4-oxopiperidinocarbonyl; $R_2$= H; $R_3$= CH$_2$SO$_2$CH$_3$; and $R_4$, $R_5$ together=—O(CH$_2$)$_3$O—)

To the product of Example 37 (50 mg) in 15 ml of chloroform was added 33 mg of m-chloroperbenzoic acid at 0° C. After stirring for 1 hour, the mixture was diluted with 50 ml of ethyl acetate and washed with a 10% sodium sulfite solution (2×50 ml) and a 0.1N sodium hydroxide solution. The organic phase was dried over magnesium sulfate, concentrated and chromatographed (methanol-methylene chloride, 8: 92, v:v) to give 18 mg of the desired sulfone.

NMR(300 MHz, CH$_3$OH-d$_4$)delta 3.06 (s, 3H), 4.08 (m, 1H), 4.49 (m, 3H) and 4.78 (m, 2H).

EXAMPLE 52

4-Oxopiperidinocarbonyl-PheSOMeCys-HACPP (OCH$_2$CH$_2$CH$_2$O) ($R_1$=4-oxopiperidinocarbonyl; $R_2$=H; $R_3$= CH$_2$SOCH$_3$; and $R_4$, $R_5$ together=—O(CH$_2$)$_3$O—)

The product of Example 37 (50 mg) in 5 ml of chloroform at 0° C. was treated with 16 mg of m-chloroperbenzoic acid and the mixture allowed to stir for 1 hour. Solid sodium sulfite (200 mg) was added, the mixture concentrated and the residue chromatographed (methanol-methylene chloride, 8:92, v:v) to give 32 mg of a 1:1 mixture of sulfoxides.

NMR(300 MHz, CH$_3$OH-d$_4$)delta 2.74 (2xs, 3H), 4.08 (m, 1H), 4.49 (m, 4H) and 4.75 (m, 3H).

EXAMPLE 53

Morpholinocarbonyl-PheNle-HACPP (OCH$_3$) (ONa) (R$_1$=morpholinocarbonyl; R$_2$= H; R$_3$=CH$_3$(CH$_2$)3—; R$_4$=OCH$_3$; and R$_5$=ONa)

A mixture of 31 mg of the product of Example 1 and 8 mg of sodium iodide in 2 ml of acetone was refluxed for 18 hours. The mixture was concentrated and the residue was triturated with diethyl ether to afford 35 mg of the desired salt.

NMR(300 MHz, D$_2$O)delta 3.62 (d, 3H), 3.70 (m, 1H), 4.18 (m, 1H), 4.28 (m, 1H) and 4.54 (m, 1H).

EXAMPLE 54

Morpholinocarbonyl-PheSMeCys-HACPP (CH$_3$)$_2$ (R$_1$=morpholinocarbonyl; R$_2$=H; R$_3$=CH$_2$SCH$_3$; and R$_4$, R$_5$=CH$_3$)

A. Boc-HACPP (CH$_3$)$_2$

A mixture of 3.23 g of dimethylphosphine oxide, 3.52 g Boc-cyclohexylalanal and 4.0 g of potassium fluoride in 10 ml of dimethylformamide was stirred at room temperature under nitrogen for 36 hours. The mixture was diluted with 500 ml of ethyl acetate and washed with water (5×100 ml). The organic layer was dried, concentrated and the residue chromatographed (methanol-methylene chloride, 7:93, v:v) to give 3.28 of the desired intermediate.

NMR(300 MHz, CDCl$_3$)delta 1.46 (s, 9H), 1.58 (d, J=12 Hz, 6H), 3.86 (m, 1H) and 3.98 (m, 1H).

B. HACPP (CH$_3$)$_2$.HCl

The product of Example 54A (230 mg) was deprotected with hydrogen chloride in dioxane as in Example 1 to give 230 mg of crude product.

NMR(300 MHz, DMSO-d$_6$)delta 1.54 (d, J=13 Hz, 3H), 1.58 (d, J=14 Hz, 3H) and 3.86 (m, 1H).

C. Boc-SMeCys-HACPP (CH$_3$)$_2$

Using the standard DEC procedure, 197 mg of Boc-SMeCys was coupled with 180 mg of the product of Example 54B. An aqueous work-up gave 245 mg of product as a 3:1 mixture of hydroxyl epimers.

NMR(300 MHz, CDCl$_3$)delta 1.46 (s, 9H), 2.15 (s, H), 3.90 (m, 1H), 4.16 (m, 1H) and 4.34 (m, 1H).

D. SMeCys-HACPP (CH$_3$)$_2$.HCl

The product of Example 54C (230 mg) was deprotected using hydrogen chloride in dioxane as in Example 1 to give 240 mg of crude product.

NMR(300 MHz, DMSO-d$_6$)delta 1.38 (d, J=12 Hz, 3H), 1.43 (d, J=13 Hz, 3H), 2.14 (s, 3H) and 3.72 (m, 1H).

E. Morpholinocarbonyl-PheSMeCys-HACPP (CH$_3$)$_2$

Morpholinocarbonyl-Phe (200 mg) was coupled with 230 mg of the product of Example 54D using the standard DEC procedure of Example 1D to give, after chromatographing (methanol-methylene chloride, 7.5:92.5, v:v), 102 mg of the desired product.

NMR(300 MHz, CDCl$_3$)delta 1.50 (d, J=12 Hz, 3H), 1.52 (d, J=12 Hz, 3H), 2.08 (s, 3H), 3.79 (m, 1H), 4.37 (m, 1H) and 4.48 (m, 2H).

EXAMPLES 55–57

Employing the procedure of Example 54 and starting with the appropriate phenyl-alanine derivative, the following analogs were prepared:

| R$_1$ | NMR(300MHz)delta |
|---|---|
| pyrrole-3-carbonyl (C(=O)— attached to 3-position of 1H-pyrrole) | (CH$_3$OH-d$_4$)1.52(d, J=12Hz, 3H), 1.54(d, J=12Hz, 3H), 2.01(s, 3H), 3.85(dd, J=3, 6Hz, 1H), 6.51(m, 1H), 6.73(m, 1H). |
| CH$_3$C(=O)— | (CDCl$_3$)1.51(d, J=12Hz, 6H), 1.92(s, 3H), 2.08(s, 3H), 3.84 (m, 1H), 4.34(m, 1H), 4.60(m, 1H), 4.77(m, 1H). |
| 4-oxopiperidine-1-carbonyl (O=C\<ring\>N—C(=O)—) | (CDCl$_3$)1.52(d, J=13Hz, 3H), 1.56(d, J=14Hz, 3H), 2.12(s, 3H), 3.80(m, 1H), 4.36(m, 1H), 4.54(m, 2H). |

EXAMPLES 58–59

Starting with the requisite dialkylphosphine oxide derivative and morpholinocarbonyl-PheSMeCys and using the procedure of Example 1F, the following compounds were prepared:

| R$_4$ | R$_5$ | NMR(300MHz)delta |
|---|---|---|
| C$_2$H$_5$ | C$_2$H$_5$ | (CDCl$_3$)2.14(brs, 3H), 3.90(m, 1H), 4.42(m, 2H), 4.51(m, 1H). |
| —(CH$_2$)$_4$— | | (CDCl$_3$)2.08(s, 3H), 4.06(m, 1H), 4.34(m, 1H), 4.44(m, 1H), 4.52(m, 1H). |

EXAMPLES 60–61

By substituting the appropriate dialkyl phosphite derivative for HACPP(CH$_3$)$_2$ in Examples 54 and 57, the following compounds were prepared:

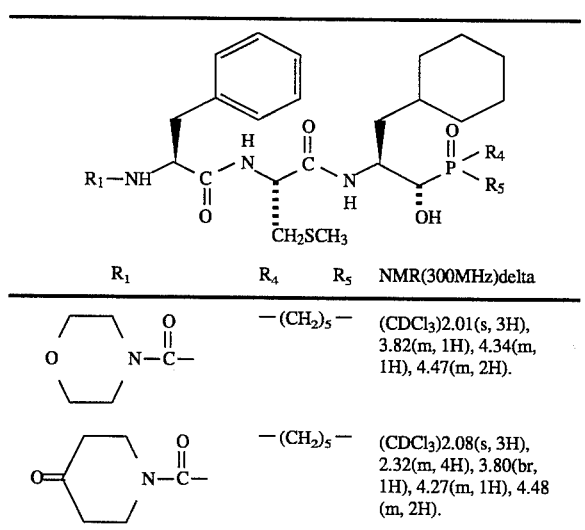

| R$_1$ | R$_4$ | R$_5$ | NMR(300MHz)delta |
|---|---|---|---|
| ![morpholinyl-C(=O)-] | —(CH$_2$)$_5$— | | (CDCl$_3$)2.01(s, 3H), 3.82(m, 1H), 4.34(m, 1H), 4.47(m, 2H). |
| ![4-oxopiperidinyl-C(=O)-] | —(CH$_2$)$_5$— | | (CDCl$_3$)2.08(s, 3H), 2.32(m, 4H), 3.80(br, 1H), 4.27(m, 1H), 4.48 (m, 2H). |

EXAMPLE 62

Morpholinocarbonyl-PheSMeCys-HACPP [N(CH$_3$)$_2$]$_2$ (R$_1$ = morpholinocarbonyl; R$_2$= H; R$_3$= CH$_2$SCH$_3$; and R$_4$, R$_5$=N(CH$_3$)$_2$)

A. CBZ-HACPP [N (CH$_3$)$_2$]$_2$

A solution of 734 mg of HPO[N(CH$_3$)$_2$]$_2$ in 10 ml of tetrahydrofuran was added at −78° C. to 1.1 equivalents of lithium diisopropylamide in 10 ml of the same solvent, and the solution allowed to warm to −50° C. over 3 hours. CBZ-cyclohexylalanal (740 mg) in 10 ml of the same solvent was added dropwise to the reaction mixture and the reaction mixture stirred for 4 hours. The reaction was quenched with a saturated ammonium chloride solution and poured into 200 ml of water and extracted with ethyl acetate (2×200 ml). The combined extracts were dried over magnesium sulfate and concentrated. The residue was chromatographed (methanol-methylene chloride, 5:95, v:v) to afford 528 mg of the desired intermediate.

NMR(300 MHz, CDCl$_3$)delta 2.60 (m, 12 H), 3.91 (m, 1H) and 4.02 (m, 1H).

B. HACPP[N(CH$_3$)$_2$]$_2$

A mixture of 355 mg of the product of Example 62A and 355 mg of 10% palladium-on-charcoal in 25 ml of methanol was shaken in a hydrogen atmosphere at a pressure of 50 psi for 3 hours. The spent catalyst was filtered and the filtrate concentrated to give 255 mg of product.

NMR(300 MHz, CDCl$_3$)delta 2.64 (m, 12H), 3.06 (m, 1H) and 3.28 (m, 1H).

C. Morpholinocarbonyl-PheSMeCys-HACPP [N (CH$_3$)$_2$]$_2$

The product of Example 62B (255 mg) was coupled with 381 mg of morpholinocarbonyl-PheSMeCys using the general procedure of Example 1F to give, after chromatographing (methanol-methylene chloride, 5:95, v:v), 35 mg of the desired more polar isomer.

NMR(300 MHz, CDCl$_3$)delta 2.13 (s, 3H), 2.65 (d, J=13 Hz, 6H), 2.68 (d, J=13 Hz, 6H), 4.17 (m, 1H), 4.25 (m, 1H), 4.43 (m, 1H) and 4.51 (m, 1H).

EXAMPLE 63

Boc-PheSMeCys-HACPP (OCH$_2$CH$_2$CH$_2$O) (R$_1$ = (CH$_3$)$_3$COCO-; R$_2$= H; R$_3$= CH$_3$SCH$_2$; and R$_4$ and R$_5$ together=—OCH$_2$CH$_2$CH$_2$O—)

The titled compound was prepared by substituting Boc-Phe for 4-oxopiperidinocarbonyl in Example 37. NMR(300 MHz, CDCl$_3$)delta 1.32 (s, 9}{), 2.05 (s, 3H), 4.00 (m, 2H), 4.30 (m, 2H), 4.45 (m, 1H), 4.58 (m, 1H), 4.72 (m, 1H) and 4.85 (m, 1H).

EXAMPLE 64

4-Oxopiperidinocarbonyl-PheNle-HACPP (OCH$_2$CH$_2$CH$_2$O) (R$_1$=4-oxopiperidinocarbonyl; R$_2$=H; R$_3$= CH$_3$(CH$_2$)$_3$—; and R$_4$ and R$_5$ together =—OCH$_2$CH$_2$CH$_2$O—)

The titled compound was prepared by substituting Boc-Nle for Boc-SMeCys in Example 37. NMR(300 MHz, CDCl$_3$)delta 3.54 (m, 4H), 4.08 (m, 2H), 4.32 (m, 2H), 4.47 (m, 1H) and 4.67 (3H).

I claim:

1. A compound of the formula

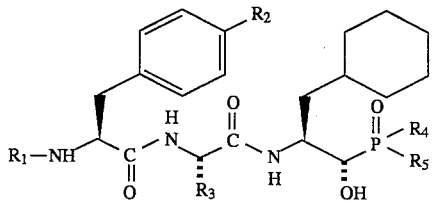

or a pharmaceutically acceptable salt thereof, wherein R$_1$ is

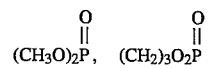

or X—Y—, where X is morpholino, N-methylpiperazino, piperidino, pyrrolidin-1-yl, pyrrolyl, 3-oxopyrrolidin-1-yl, imidazolyl, cis-4-hydroxycyclohexyl, trans-4-hydroxycyclohexyl, acetylalkyl having three to six carbon atoms, alkyl having one to three carbon atoms, 4-oxopiperidino, 4-oxocyclohexyl, alkoxy having one to five carbon atoms or 4-hydroxypiperidino and Y is

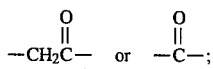

R$_2$ is hydrogen or methoxy; R$_3$ is alkyl having one to four carbon atoms, methoxyalkyl said alkyl having one to three carbon atoms, methythioalkyl said alkyl having one to three carbon atoms, hydroxymethyl, imidazol-4-ylmethyl, methylsulfonylmethyl, methylsulfinylmethyl or carbamylethyl; R$_4$ and R$_5$ when considered separately are each alkyl having one to three carbon atoms, benzyloxy, alkoxy having one to four carbon atoms, dimethylamino or hydroxy; and R$_4$ and R$_5$ when taken together are alkylene having four to six carbon atoms, alkylenedioxy having three to four carbon atoms or mono- or dimethylalkylenedioxy having four to six carbon atoms.

2. A compound of claim 1, wherein $R_1$ is X—Y— where X is morpholino, Y is

$R_3$ is methylthioalkyl said alkyl having one to three carbon atoms and $R_2$ is hydrogen.

3. The compound of claim 2, wherein $R_3$ is methylthiomethyl, $R_4$ is methoxy and $R_5$ is isopropoxy.

4. The compound of claim 2, wherein $R_3$ is methylthiomethyl and $R_4$ and $R_5$ taken together are propylenedioxy.

5. The compound of claim 2, wherein $R_3$ is methylthiomethyl and $R_4$ and $R_5$ taken together are butylene.

6. A compound of claim 1, wherein $R_1$ is X—Y— where X is 4-oxopiperidino, Y is

$R_2$ is hydrogen and $R_3$ is methylthioalkyl said alkyl having one to three carbon atoms.

7. The compound of claim 6, wherein $R_3$ is methylthiomethyl and $R_4$ and $R_5$ are each methoxy.

8. The compound of claim 6, wherein $R_3$ is methylthiomethyl and $R_4$ and $R_5$ taken together are propylenedioxy.

9. The compound of claim 6, wherein $R_3$ is methylthiomethyl and $R_4$ and $R_5$ taken together are pentylene.

10. A compound of claim 1, wherein $R_1$ is X—Y— where X is morpholino, Y is C=O, $R_2$ is hydrogen and $R_3$ is alkyl having one to four carbon atoms.

11. The compound of claim 10, wherein $R_3$ is n-butyl and $R_4$ and $R_5$ are each methoxy.

12. A compound of claim 1, wherein $R_1$ is X—Y— where X is 4-oxopiperidino, Y is

$R_2$ is hydrogen and $R_3$ is alkyl having one to four carbon atoms.

13. The compound of claim 12, wherein $R_3$ is n-butyl and $R_4$ and $R_5$ taken together are propylenedioxy.

14. A method of treating hypertension in a mammal which comprises administering to said mammal an anti-hypertensive effective amount of a compound according to claim 1.

15. A pharmaceutical composition comprising an anti-hypertensive effective amount of a compound according to claim 1 and a pharmaceutically acceptable diluent or carrier.

* * * * *